(12) United States Patent
Masotti et al.

(10) Patent No.: US 8,113,209 B2
(45) Date of Patent: Feb. 14, 2012

(54) SUB-DERMAL LASER SKIN TREATMENT

(75) Inventors: Leonardo Masotti, Florence (IT); George E. S. Cho, Hopkinton, MA (US)

(73) Assignees: Cynosure, Inc., Westford, MA (US); EL. EN. S.p.A., Calenzano (FI) (IT)

( * ) Notice: Subject to any disclaimer, the term of this patent is extended or adjusted under 35 U.S.C. 154(b) by 1116 days.

(21) Appl. No.: 11/704,710

(22) Filed: Feb. 9, 2007

(65) Prior Publication Data

US 2007/0219540 A1    Sep. 20, 2007

Related U.S. Application Data

(63) Continuation-in-part of application No. 11/099,216, filed on Apr. 5, 2005, now Pat. No. 7,975,702.

(51) Int. Cl.
*A61B 19/00* (2006.01)

(52) U.S. Cl. .......... 128/898; 606/3; 606/15; 607/89; 607/92

(58) Field of Classification Search .......... 607/88, 607/89, 92, 100–102; 606/3, 13–16, 130; 128/898; 604/19–22
See application file for complete search history.

(56) References Cited

U.S. PATENT DOCUMENTS

| | | | |
|---|---|---|---|
| 5,102,410 A * | 4/1992 | Dressel ............... | 606/15 |
| 5,343,543 A | 8/1994 | Novak et al. | |
| 5,495,541 A | 2/1996 | Murray et al. | |
| 5,871,479 A | 2/1999 | Furumoto et al. | |
| 5,954,710 A | 9/1999 | Paolini et al. | |
| 6,106,516 A | 8/2000 | Massengill | |
| 6,203,540 B1 | 3/2001 | Weber | |
| 6,206,873 B1 * | 3/2001 | Paolini et al. ............ | 606/7 |
| 6,235,017 B1 | 5/2001 | Jegorov et al. | |
| 6,254,597 B1 | 7/2001 | Rizoiu et al. | |
| 6,464,694 B1 | 10/2002 | Massengill | |
| 6,508,813 B1 | 1/2003 | Altshuler | |
| 6,511,475 B1 | 1/2003 | Altshuler et al. | |
| 6,517,532 B1 | 2/2003 | Altshuler et al. | |
| 6,562,054 B1 | 5/2003 | Weber et al. | |
| 6,605,079 B2 * | 8/2003 | Shanks et al. ............ | 606/2 |
| 6,605,080 B1 | 8/2003 | Altshuler et al. | |

(Continued)

FOREIGN PATENT DOCUMENTS

DE    103 20 984 A1    12/2004

(Continued)

OTHER PUBLICATIONS

Promotional Materials for Omega Engineering, Inc., 4 pp. dated 1995.

(Continued)

*Primary Examiner* — Ahmed Farah
(74) *Attorney, Agent, or Firm* — Hamilton, Brook, Smith & Reynolds, P.C.

(57) ABSTRACT

A method and system for skin tightening comprises a hollow cannula that contains an optical fiber connected to a laser source. The cannula is inserted subcutaneously into a patient so that the end of the fiber is located within the tissue underlying the dermis. The source emits an output pulse that is conveyed by the fiber to the dermis, where the pulse causes collagen destruction and shrinkage within the treatment area. Radiation from the skin surface is detected to prevent non-reversible damage to the dermis, such as skin necrosis and excessive collagen melting. This method of sub-cutaneous laser treatment can also be used to treat striae, or stretch marks.

35 Claims, 4 Drawing Sheets

U.S. PATENT DOCUMENTS

| | | | |
|---|---|---|---|
| 6,653,618 | B2 | 11/2003 | Zenzie |
| 6,663,620 | B2 | 12/2003 | Altshuler et al. |
| 6,723,090 | B2 | 4/2004 | Altshuler et al. |
| 6,746,473 | B2 | 6/2004 | Shanks et al. |
| 7,217,265 | B2 | 5/2007 | Hennings et al. |
| 7,524,316 | B2 * | 4/2009 | Hennings et al. ............... 606/7 |
| 2001/0025190 | A1 | 9/2001 | Weber et al. |
| 2002/0038121 | A1 | 3/2002 | Rozenberg et al. |
| 2003/0167053 | A1 | 9/2003 | Taufig |
| 2004/0186469 | A1 | 9/2004 | Woloszko et al. |
| 2006/0224148 | A1 | 10/2006 | Cho et al. |
| 2006/0265032 | A1 | 11/2006 | Hennings et al. |
| 2007/0142881 | A1 * | 6/2007 | Hennings ..................... 607/89 |
| 2007/0293849 | A1 * | 12/2007 | Hennings et al. ............... 606/9 |
| 2008/0188835 | A1 * | 8/2008 | Hennings et al. ........... 604/542 |
| 2008/0306476 | A1 * | 12/2008 | Hennings et al. .............. 606/27 |

FOREIGN PATENT DOCUMENTS

| | | |
|---|---|---|
| WO | WO 91/12774 | 9/1991 |
| WO | WO 97/37723 | 10/1997 |
| WO | WO 98/14159 | 4/1998 |
| WO | WO 99/22656 | 5/1999 |
| WO | WO 01/39834 A1 | 6/2001 |
| WO | WO 01/45580 | 6/2001 |
| WO | WO 01/49194 A2 | 7/2001 |
| WO | WO 01/91827 A1 | 12/2001 |
| WO | WO2006/107522 | 10/2006 |

OTHER PUBLICATIONS

DEKA Medical Electronic Laser Associated, SMARTLIPO Operative Manual, dated Feb. 19, 2001.

Neira, Rodrigo, et al., "Fat Liquefaction: Effect of Low-Level Laser Energy on Adipose Tissue," *Plastic and Reconstructive Surgery*, 110(3): 912-925 (2002).

Apfelberg, David B., "Results of Multicenter Study of Laser-Assisted Liposuction," *Body Contouring*, 23(4): 713-719 (1996).

Goldman, Alberto, et al., "Laserlipolysis: Liposuction Using Nd-YAG Laser," *Rev. Soc. Bras. Cir. Plast.*, 17(1): 17-26 (2002).

Badin, A.Z.D., et al., "Laser Lipolysis: Flaccidity Under Control," *Aesth. Plast. Surg.*, 26: 335-339 (2002).

"What is Liposuction?" Liposuction Information from U.S. Food and Drug Administration: Center for Devices and Radiological Health (CDRH) web site (Updated: Aug. 1, 2002).

DEKA, Medical Electronic Laser Associated, SMARTLIPO, Smartlaserline, 2 page description.

MicroGroup Brochure, pp. 6, MicroGroup, Inc., Medway, MA.

Protest and third party submission in published application under 39 C.F.R. §1.291 served on Jun. 17, 2008.

European Search Report for foreign application No. EP 08 16 2477, dated Oct. 7, 2008.

Office Action from U.S. Appl. No. 11/099,216, mailed Dec. 11, 2009.

International Preliminary Report on Patentability and Written Opinion for PCT/US2006/009006; issued Oct. 9, 2007.

Final Office Action dated Aug. 26, 2010 for U.S. Appl. No. 11/099,219.

Office Action dated Dec. 22, 2010, for U.S. Appl. No. 11/099,216.

Notice of Allowance dated Mar. 16, 2011 for U.S. Appl. No. 11/099,216.

\* cited by examiner

SUB-DERMAL LASER SKIN TREATMENT

RELATED APPLICATION

This application is a continuation-in-part of U.S. application Ser. No. 11/099,216, filed Apr. 5, 2005 now U.S. Pat. No. 7,975,702, the entire teachings of which are incorporated herein by reference.

BACKGROUND OF THE INVENTION

Plastic surgeons, dermatologists and their patients continually search for new and improved methods for treating the effects of an aging skin. One common procedure for rejuvenating the appearance of aged or photodamaged skin is laser skin resurfacing using a carbon dioxide laser. Another technique is non-ablative laser skin tightening, which does not take the top layer of skin off, but instead uses a deep-penetrating laser to treat the layers of skin beneath the outer epidermal layer, tightening the skin and reducing wrinkles to provide a more youthful appearance.

In skin tightening treatment, a laser system is operated to deliver a pulse of radiation to the external surface of the patient's skin. The parameters of the pulse are chosen such that energy from the pulse will penetrate the outer epidermal layer of the skin, into the underlying dermal layer, where at least a portion of the energy will be absorbed by the collagen matrix within the dermis. By selecting the proper laser parameters and techniques for the laser treatment, the deeper region of the skin tissue can be heated to a temperature sufficient to shrink the collagen in the dermal layer, thereby tightening the skin and reducing wrinkles and laxity of the skin to provide a more youthful appearance.

SUMMARY OF THE INVENTION

With existing techniques for laser skin tightening treatment, it has been difficult to control the depth and amount of energy delivered to the collagen without also damaging or killing the dermal cells. Much of the energy of the treatment pulse is wasted due to scattering and absorption in the outer epidermal layer, and the relatively high pulse energy required to penetrate this outer layer can cause pain and epidermal damage.

Accordingly, in one aspect, a method and system for skin tightening comprises a hollow tubular cannula that contains an optical fiber connected to a laser source. The cannula is inserted subcutaneously into a patient so that the end of the fiber is located within the tissue underlying the dermis. The source emits an output pulse that is conveyed by the fiber to the dermis, where the pulse causes collagen shrinkage within the treatment area, thus tightening the skin.

In one embodiment, the laser source is a near infrared laser, such as an Nd:YAG laser, which emits a pulsed beam having a wavelength between approximately 0.70 and 3.00 µm, even more preferably between about 0.75 and 2.05 µm, and even more preferably between about 0.8 and 1.55 µm, an energy between about 30 and 600 mjoules per pulse, a pulse frequency between about 5 and 100 Hz, and an average power between about 1 and 20 watts. The hollow cannula is generally between 2 and 10 inches in length, and can have an external diameter of between about 1 and 2 mm. A second "aiming" laser, which emits visible light that is coupled into the optical fiber, can be employed to assist the operator in locating the tip of the cannula underneath the patient's skin.

In certain embodiments, the cannula can include a curved or bent section at its distal end to help direct the radiation from the optical fiber into the patient's lower dermis. In other embodiments, the optical fiber can comprise a side-firing fiber that directs the radiation into the dermis.

A radiation detector can be arranged to detect radiation from the surface of the skin above the tip of the fiber. The radiation detector can be, for example, a temperature sensor which detects a temperature rise in the dermis of the patient. The temperature sensor is thus able to warn the operator of potentially harmful temperatures in the underlying dermal layers. Alternatively, the radiation detector can be an optical sensor that detects the intensity of light transmitted through the patient's skin. Thus, when used in conjunction with an "aiming" laser which emits a visible laser beam from the tip of the cannula, the optical sensor can warn the operator when the optical fiber is delivering excessive energy to the patient's skin. In other embodiments, the operator can directly monitor by eyesight the intensity of the visible light from the aiming laser emitted through the patient's skin. In still other embodiments, the operator can pass his or her hand or finger through the area of the skin above the treatment area to monitor skin surface temperature and detect the presence of potentially harmful temperatures in the underlying dermal layers.

According to yet another embodiment, a temperature sensitive material is applied to the surface of the patient's skin above the treatment area. For example, the temperature sensitive material can be adapted to change color in response to a rise in temperature on the patient's skin, thus warning the operator of potentially harmful temperatures in the lower dermal region.

The method and system of the present invention enables the collagen in dermal layer to be treated directly by laser radiation, without the need for the radiation to penetrate the outer epidermis. This enables greater efficiency in the energy delivered to the targeted collagen, and less pain and visible injuries to the epidermis. The method of the invention treats the skin in an "inside-out" fashion, which allows more effective treatment of deeper-lying areas of dermal layer. The method is furthermore minimally-invasive. Using a small diameter cannula, the entry slit for the cannula can also be made very small (e.g. 1-2 mm), so that no suturing of the slit is required post-treatment. In certain embodiments, the cannula itself can make the incision in the patient's skin, and no additional instruments are necessary.

The method of the invention can be used in conjunction with conventional laser skin tightening treatment where the treatment beam is directed to the external surface of the skin. The method can also be used in conjunction with other invasive treatment methods, such as laser lipolysis treatment, where a cannula containing an optical fiber connected to a laser source is inserted into the fatty adipose layer underlying the dermis to heat up and liquefy adipose cells. In certain embodiments, the same laser system and cannula can be used for both laser lipolysis treatment and sub-dermal skin tightening treatment.

According to yet another aspect of the invention, a method and system for treatment of striae (stretch marks) comprises a hollow tubular cannula, such as a cannula, that contains an optical fiber connected to a laser source. The cannula is inserted subcutaneously into a patient so that the end of the fiber is located within the tissue underlying the affected area of the dermis. The source emits an output pulse that is conveyed by the fiber to the dermis, where the pulse causes collagen shrinkage within the treatment area, and reduces the appearance of striae on the patient's skin.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Figure 1:
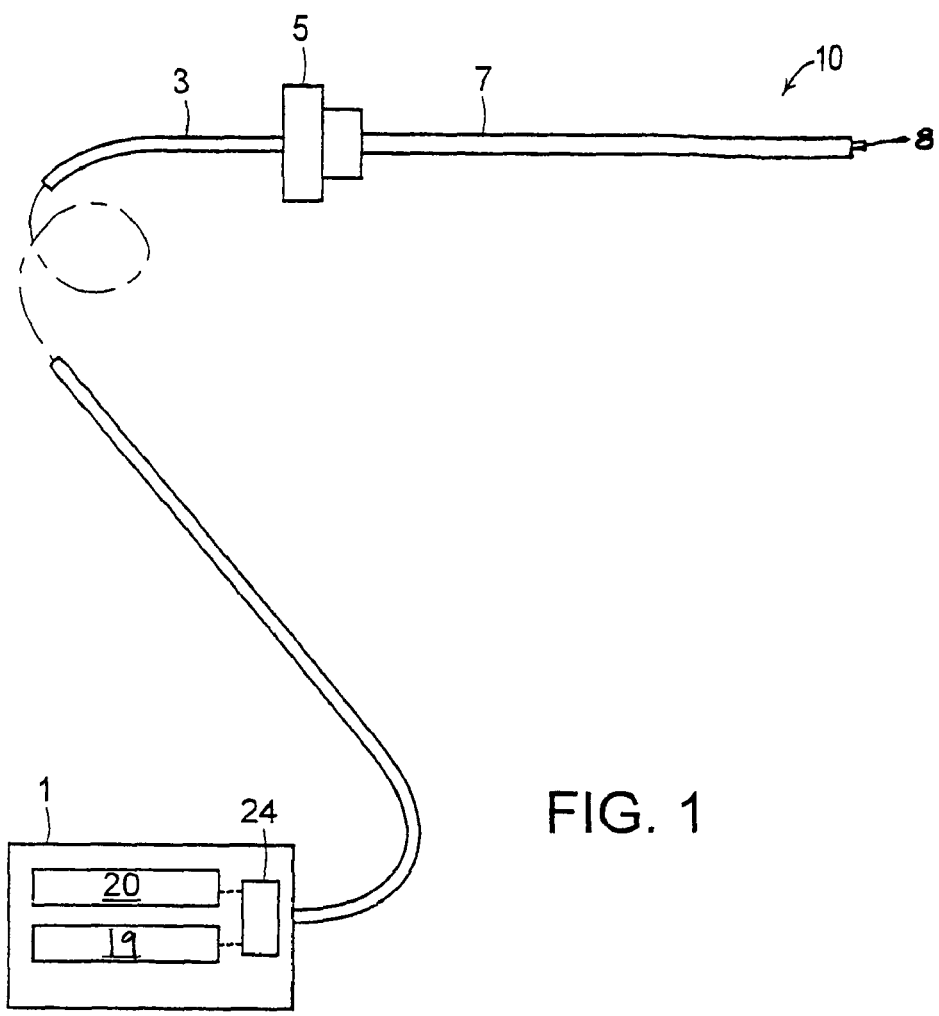
FIG. 1 is a schematic diagram of the laser lipolysis system of the invention.

A description of preferred embodiments of the invention follows. With reference initially to FIG. 1, the device comprises a laser source 1 coupled to an optical fiber 3. The fiber 3 connects to a hollow cannula 7, and extends through the interior of the cannula 7, terminating at or near the cannula tip. Preferably, the proximal end of the fiber 3 protrudes out from the tip of the cannula 7 by approximately 1-2 mm. The fiber 3 can be connected to the cannula 7 using any conventional means, such as a Touhy-Borst connector 5, which holds the fiber tight within the cannula. In operation, laser energy from the source 1 is coupled into the fiber 3, and is conveyed along the length of the fiber to the cannula tip. The laser energy can thus be directed from the end of the fiber to a treatment site by controlling the location and orientation of the cannula tip.

Figure 3A:
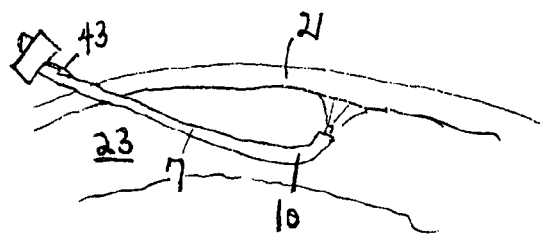
FIG. 3A is a cross-sectional side-view of the treatment area of a patient containing a cannula having a curved portion in accordance with the invention.

The cannula 7 is a thin tubular structure, that is preferably made from stainless-steel. Generally, the cannula has an external diameter of between about 1 to 2 mm. Smaller-diameter cannulas can also be used. The length of the cannula can vary depending upon the particular skin tightening therapy, although typically the cannula will be between about 2 and 10 inches long. In certain embodiments, such as shown in FIG. 3A, the cannula 7 can include a curve or bend 10 at its distal end, the purpose of which will be described in more detail below. In other embodiments, the cannula 7 is a straight cannula, such as shown in FIG. 1.

Optical fiber delivery systems for laser light are well-known. In general, the optical fiber of the present invention has a core diameter of less than about 1000 μm, and preferably about 300 μm. The fiber is inserted into and through the cannula 7 at the connector 5 until it exits from the tip of the cannula. The connector 5 typically includes a nut that is tightened against a rubber or elastomeric grommet to secure the fiber in place. As an alternative or in addition to the connector 5 shown in FIG. 1, a larger handpiece connected to the base of the cannula could also be employed.

In the embodiment of FIG. 1, the laser source 1 comprises a treatment laser 20, which in one embodiment is an Nd:YAG laser. The light emitted from the laser 20 is coupled into the optical fiber 3. In this manner, the optical fiber 3 conveys to the point of the cannula 7 a treatment laser beam. The treatment laser 20 emits a beam which is preferably pulsed, at a wavelength between 0.70 and 3.00 μm, for example at 1.06 μm, with an energy level between 30 and 600 mjoules per pulse, and an average power between about 1 and 20 watts. The wavelength is preferably between 0.8 and 1.55 μm.

The parameters of the laser treatment pulse are designed to promote collagen shrinkage within the dermis. The use of laser radiation to heat collagen molecules within the skin to the thermal shrinkage temperature is described in, for example, International Published Patent Application No. WO97/37723, the entire teachings of which are incorporated herein.

The device of the present invention is used as follows: an entry slit for the cannula is made by inserting a sharp-tip, surgical blade (e.g., a Number 11 blade) through the outer epidermal and dermal layers and into underlying layer of fat tissue. Preferably, the entry slit is about 1 to 2 mm long. It will be understood that the cannula itself can have a sharp tip for forming the entry hole in the patient's skin.

Figure 2:
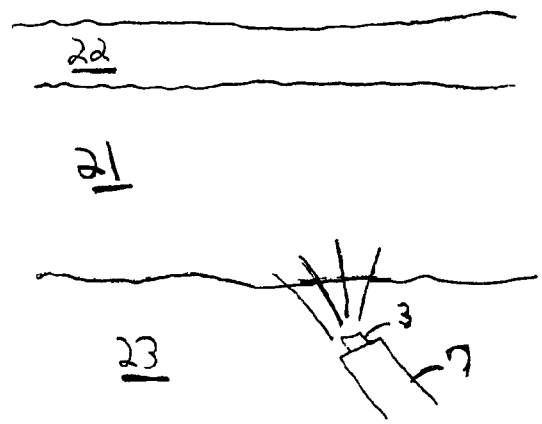
FIG. 2 is a cross-sectional side-view of the treatment area of a patient containing an optical fiber cannula.

The cannula 7 then is inserted through the entry slit into the subcutaneous layer underlying the treatment area. The fiber 3 can be pre-loaded into the cannula 7 before the cannula is inserted into the entry slit. Alternatively, the fiber can be fed into the cannula after the cannula has been inserted into the patient. As shown in FIG. 2, the tip of the cannula 7 is located underneath and directed at the area of the dermis 21 to be treated. Generally, the tip of the cannula is located within the layer of fatty tissue 23 underlying the dermis 21. The laser beam, in the appropriate dosage, is directed at the dermis 21 to heat the collagen matrix within the dermal layer to the thermal shrinkage temperature which is generally between about 55 and 70 degrees Celsius. This causes the collagen matrix to shrink without losing its structural integrity, and tightens the skin. This process can also stimulate the fibroblasts to manufacture new collagen, further enhancing the skin's appearance. Preferably, the energy from the laser is insufficient to cause permanent damage to the cells of the dermis, including skin necrosis and melting of substantial amounts of collagen. The laser pulse can also promote hemostasis in the tissue to minimize internal bleeding. The resultant shrinking of collagen tightens the skin to eliminate wrinkles and provide a more youthful appearance.

In practice, the cannula 7 is initially inserted subcutaneously and is then moved to various locations by the operator for the time which is necessary according to the characteristics of the tissue. Typically, the needle is kept in each penetration hole for a few minutes. By extracting the cannula and inserting it subcutaneously in an adjacent position, a subsequent portion of tissue is treated. From one and the same entry hole, the cannula 7 can be inserted in various radial directions, treating an entire area of the tissue.

Following the skin tightening treatment of the invention, the cannula 7 and optical fiber 3 are withdrawn from the body through the entry slit. An advantage of the present technique is that the entry slit for the laser cannula can be made so small, no suturing of the slit is required post-treatment.

In certain embodiments, the operator can locate the position of the cannula tip 33 by virtue of an aiming laser 19, which projects visible light from the cannula tip through the overlying dermal 21 and epidermal 22 layers. The aiming laser 19 is operatively connected with the optical fiber 3, and emits a beam of non-treatment visible radiation to provide the operator a visible indication of both the location of the cannula tip 33 and an estimate of the depth of the tip vis-a-vis the interior surface of the dermis. Both the aiming laser beam 19 and the treatment laser beam 20 can be coupled into the optical fiber 3 by a beam combiner 24.

In certain embodiments, the cannula 7 can comprise a curved or bent portion 10, as shown in FIG. 3A. The curved portion 10 is located at the distal end of the cannula, and enables the cannula to more easily direct laser energy out into the lower dermis. As shown in FIG. 3A, for example, the distal end of the cannula 7 has an upward curve. It will be understood that the curved portion can be a gradual curve (as shown in FIG. 3A), or could be a sharper, angular bend.

Figure 3B:
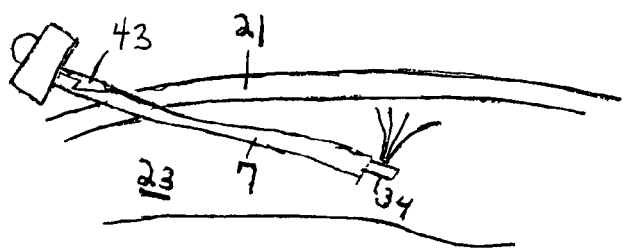
FIG. 3B is a cross-sectional side-view of the treatment area of a patient containing a cannula with a side-firing fiber in accordance with one embodiment of the invention.

In another embodiment, shown in FIG. 3B, a straight cannula 27 is used in conjunction with a side-firing fiber 34 that directs substantially all of the laser energy emitted from the tip of the fiber directly into the dermis. Side-firing fibers are well-known in the art, and include, for example, fibers having a small angled mirror at the tip of the fiber, fibers having a polished tip, or any other means to direct the laser output beam in a pre-determined direction. It will also be understood that a side-firing fiber 34 could also be used in conjunction with a cannula having a curved portion, as shown in FIG. 3A.

In another aspect, the cannula 7 of the invention includes a visible marker 43 that indicates to the operator the direction of the curvature or bend of the curved portion 10. Since during operation, the curved portion is typically located under the patient's skin, the marker 43 assists the user in determining which direction the tip of the cannula is directed. The marker 43 could be, for example, an arrow which points in the direction of curvature of the curved portion. The marker is preferably located at the base of the cannula, or on the connector. In the case of a cannula with a side-firing fiber, as shown in FIG. 3B, the marker 43 can indicate in which direction the fiber emits laser light.

Figure 4:
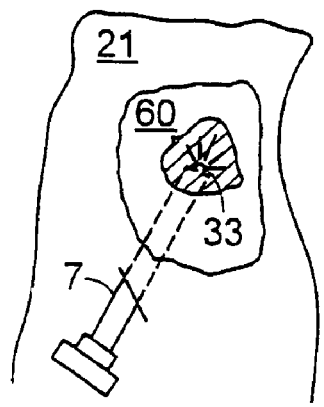
FIG. 4 illustrates a laser lipolysis treatment with a temperature sensitive material being applied to the surface of the patient's skin.

Another embodiment is shown in FIG. 4. In this embodiment, a temperature sensitive material is applied to the patient's skin over the treatment area. As shown in FIG. 4, the cannula 7 is inserted into the patient for laser lipolysis treatment. The application of the relatively high-energy treatment beam into the lower dermis, causes the temperature at the surface of the patient's skin to increase. A temperature sensitive material 60 is applied on the surface of the skin 21. The rise in temperature causes a noticeable chemical change to the material 60, such as a change in color (indicated by hatched region in FIG. 4). This change in color warns the operator when the temperature in the dermis has risen to a potentially damaging level. Examples of suitable temperature sensitive materials include thermal chromic markers, such as the OMEGALAQ® Temperature Indicating Liquid, from Omega Engineering, Inc, of Stamford, Conn.

Figure 5:
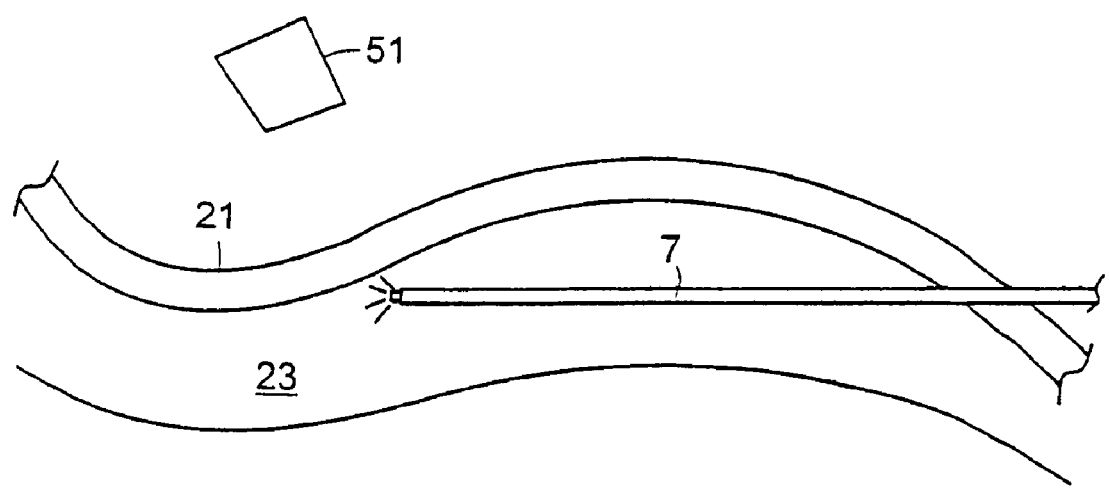
FIG. 5 is a cross-sectional side-view of the treatment area of a patient including a radiation detector above the treatment area.

Turning now to FIG. 5, yet another embodiment of the invention is shown. In this embodiment, a radiation detector 51 is positioned above the treatment area of the patient. Preferably, the detector 51 is aimed to detect radiation from the surface of the skin directly above the subcutaneous cannula tip 33. In certain embodiments, the detector 51 can be physically connected to cannula 7 in such a manner so as to ensure that the detector is properly positioned to detect radiation from the tip of the cannula. For example, the detector 51 can be positioned at the distal end of an arm (not shown), where the base of the arm is connected to the cannula 7 or to the connector 5. In other embodiments, the detector 51 is not connected to the cannula, and the operator positions the detector to detect radiation from the cannula tip 33. The operator can adjust the position and/or orientation of the detector in response to the location on the patient's skin of the visible light from the aiming beam. In one embodiment, the detector 51 can be worn by the operator on a head-strap or other item of headgear (not shown), so that when the operator looks toward the spot of light from the aiming beam, the detector 51 will automatically be aimed toward the cannula tip 33.

In one embodiment, the detector 51 is a temperature sensor that detects the temperature of the skin directly above the cannula tip 33. The detector 51 is programmed to detect a temperature rise at the skin surface resulting from the treatment of the dermis. The detector 51 can thus be programmed to warn the operator when the temperature at the surface of the skin has risen to a level that is indicative of potentially harmful temperatures in the lower dermis. Thus, the operator then knows to reduce the energy provided by the treatment beam, such as by moving the cannula 7 back away from the dermal layer.

In an alternative embodiment, the detector 51 is an optical sensor that detects the brightness of the visible light from the aiming laser emitted through the patient's skin. As in the embodiment where the detector is a temperature sensor, an optical sensor can be programmed to warn the operator when the intensity of the aiming beam rises to a level which indicates a potentially harmful temperature within the dermis.

The laser skin tightening treatment advantageously be used in conjunction with a laser lipolysis treatment, such as disclosed in co-pending International Application No. PCT/US2006/009006, filed Mar. 10, 2006, and in U.S. application Ser. No. 11/099,216, filed on Apr. 5, 2005, the entire teachings of both of which are incorporated herein by reference. The system described herein for laser skin tightening can advantageously also be utilized for laser lipolysis treatment. For example, the curved cannula and side-firing fiber embodiments of FIGS. 3A and 3B can be used for laser lipolysis treatment, where the output beam is directed towards the adipose layer and away from the dermis, and then can be turned over for skin tightening treatment, where the output beam is directed at the dermis. The marker 43 can be located on two opposing sides of the cannula to indicate the direction in which the fiber is aimed, thus permitting the operator to easily switch between the two modes of treatment-lipolysis and skin tightening.

Figure 6:
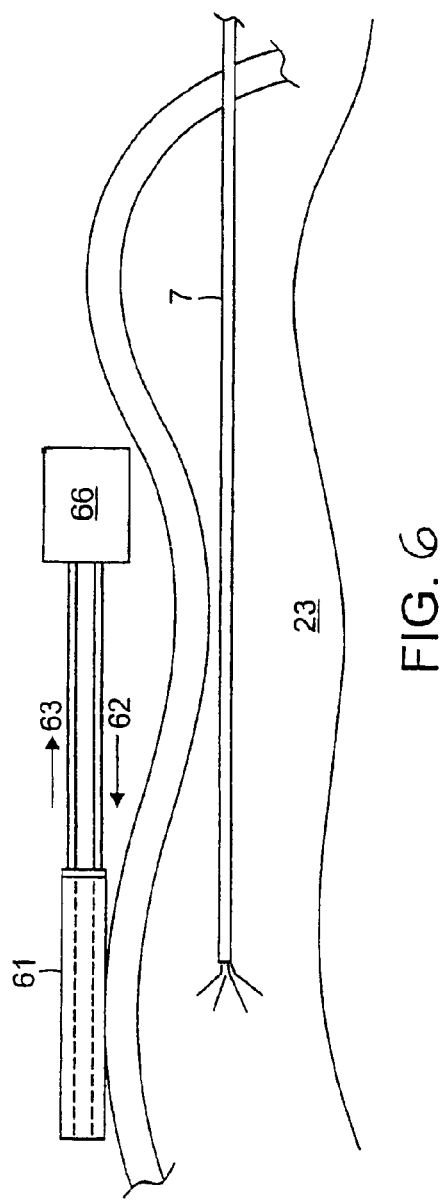
FIG. 6 illustrates a laser lipolysis treatment with a transparent contact cooling element located on the surface of the patient's skin.
Figure 7:
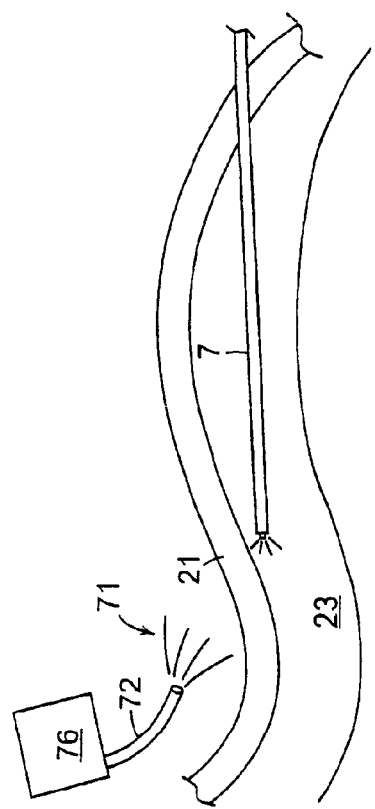
FIG. 7 illustrates a laser lipolysis treatment with chilled air being applied to the surface of the patient's skin.

Turning now to FIG. 6, a laser skin tightening system and method of the invention includes a contact cooling element 61 that is located on the surface of the patient's skin overlying the treatment area. The cooling element 61 cools the patient's dermis so as to reduce the temperature rise due to laser radiation from inside the skin, and thereby minimize damage to the patient's dermis. In one embodiment, the contact cooling element 61 is connected to a cooling unit 66 by inlet line 62 and outlet line 63. The cooling unit 66 circulates a cooling fluid through line 62 to the cooling element 61, and back through outlet line 63. The contact cooling element 61 can be made transparent to allow for the detection of radiation from the surface of the skin above the tip of the fiber, as in the embodiment shown in FIG. 5. In an alternative embodiment, shown in FIG. 7, a stream of chilled air 71 can be applied to the surface of the skin above the treatment area, for example, using a cooling unit 76 connected to a hose 72.

In addition to the skin tightening treatment described above, the present invention can also be used to treat striae, also known as stretch marks. In this treatment, the cannula is inserted into the patient's skin so that the tip of the cannula lies underneath the affected area of the patient's skin. The output laser beam is directed at the lower dermis of the patient to shrink the collagen. This helps minimize the appearance of striae on the patient's skin. It has been found that striae can be reduced by heating the dermis in the striae-affected area to the thermal shrinkage temperature for collagen, which is generally between 55 and 70 degrees Celsius.

While this invention has been particularly shown and described with references to example embodiments thereof, it will be understood by those skilled in the art that various changes in form and details may be made therein without departing from the scope of the invention encompassed by the appended claims.

While this invention has been particularly shown and described with references to example embodiments thereof, it will be understood by those skilled in the art that various changes in form and details may be made therein without departing from the scope of the invention encompassed by the appended claims.

What is claimed is:

1. A method for skin tightening, comprising:
   creating an entry hole on a patient's skin;
   subsequently inserting a blunt tip of a hollow cannula through the entry hole into a region of tissue underlying the dermal layer of the patient;
   providing an optical fiber within the cannula, the optical fiber terminating in the vicinity of the blunt tip of the cannula; and
   generating a treatment laser beam, the treatment laser beam being conveyed through the optical fiber and directed into the dermal layer, the wavelength and energy of the treatment beam being selected to heat collagen matrix within the dermal layer to a temperature between about 55 and 70 degrees Celsius and to cause collagen shrinkage within the dermal layer.

2. The method of claim 1, wherein the optical fiber is introduced into the cannula prior to inserting the cannula into the patient.

3. The method of claim 1, wherein the optical fiber is introduced into the cannula subsequent to inserting the cannula into the patient.

4. The method of claim 1, wherein the treatment beam is generated using an Nd:YAG laser.

5. The method of claim 1, wherein the wavelength of the treatment beam is between 0.70 and 3.0 μm.

6. The method of claim 1, wherein the cannula has an outer diameter of between approximately 1 and 2 mm.

7. The method of claim 1, wherein the cannula is between approximately 2 and 10 inches in length.

8. The method of claim 1, wherein the cannula comprises a curved or bent portion near the distal end of the cannula to direct laser radiation at the dermal layer.

9. The method of claim 1, wherein the optical fiber comprises a side-firing fiber to direct laser radiation at the dermal layer.

10. The method of claim 1, further comprising:
    removing the cannula from the patient and closing the entry hole without the use of a suture.

11. The method of claim 1, wherein the optical fiber protrudes from the tip of the cannula by approximately 1 to 2 mm.

12. The method of claim 1 further comprising detecting thermal radiation from the surface of the patient's skin above the treatment area, the thermal radiation being indicative of the temperature of the patient's skin within the treatment area, to prevent non-reversible damage to the dermis.

13. The method of claim 12, wherein detecting radiation comprises generating an aiming laser beam, the aiming laser beam being conveyed through the optical fiber to allow transcutaneous vision of the tip of the cannula, and wherein the detected radiation comprises visible light.

14. The method of claim 13, wherein the visible light is detected with an optical sensor.

15. The method of claim 13, wherein the visible light is detected by operator eyesight.

16. The method of claim 12, wherein detecting radiation comprises applying a temperature sensitive material to the surface of the patient's skin above the treatment area.

17. The method of claim 16, wherein the temperature sensitive material undergoes a noticeable chemical change in response to a change in the temperature of the patient's skin.

18. The method of claim 17, wherein the noticeable chemical change comprises a change in color.

19. The method of claim 16, wherein the temperature sensitive material is adapted to warn an operator when the dermis of the patient reaches harmful temperatures.

20. The method of claim 12, wherein the thermal radiation is detected with a temperature sensor.

21. The method of claim 12, wherein the thermal radiation is detected by passing a hand or finger through the area of the skin above the treatment area to monitor skin surface temperature.

22. The method of claim 12 further including:
    reducing energy provided by the treatment laser beam in response to the detected thermal radiation to prevent non-reversible damage to the dermis.

23. The method of claim 22 wherein reducing energy provided by the treatment laser beam includes moving the cannula in response to the detected thermal radiation to prevent non-reversible damage to the dermis.

24. The method of claim 1, further comprising directing a second treatment beam to the external surface of the skin, the wavelength and energy of the second treatment beam being selected to cause collagen shrinkage within the dermal layer.

25. The method of claim 24, wherein both the first and second treatment beams are applied to the skin simultaneously.

26. The method of claim 1, wherein at least one treatment beam is directed into the adipose layers to cause rupturing of the adipose cells while the cannula is inserted into the region of tissue.

27. The method of claim 1, wherein the structural integrity of the collagen is not lost.

28. The method of claim 1 further including:
    cooling the dermis to prevent non-reversible damage to the dermis.

29. The method of claim 28 wherein cooling the dermis to prevent non-reversible damage to the dermis includes applying a contact cooling element to the surface of the patient's skin.

30. A method for treating striae, comprising:
    creating an entry hole on a patient's skin;
    subsequently inserting a blunt tip of a hollow cannula through the entry hole into a region of tissue underlying the dermal layer of the patient;
    providing an optical fiber within the cannula, the optical fiber terminating in the vicinity of the blunt tip of the cannula; and
    generating a treatment laser beam, the treatment laser beam being conveyed through the optical fiber and directed into the dermal layer of a striae-containing region of the patient's skin, the wavelength and energy of the treatment beam being selected to heat collagen matrix within the dermal layer to a temperature between about 55 and 70degrees Celsius and to cause collagen shrinkage within the dermal layer and reduce the appearance of striae on the patient's skin.

31. The method of claim 30, wherein the treatment beam is generated using an Nd:YAG laser.

32. The method of claim 30, wherein the wavelength of the treatment beam is between 0.70 and 3.0 μm.

33. The method of claim 30, wherein the cannula has an outer diameter of between approximately 1 and 2 mm.

34. The method of claim 30, wherein the cannula is between approximately 2 and 10 inches in length.

35. A method for skin tightening, comprising:
creating an entry hole on a patient's skin;
inserting a hollow cannula through the entry hole into a region of tissue underlying the dermal layer of the patient;
providing an optical fiber within the cannula, the optical fiber terminating in the vicinity of the tip of the cannula;
generating a first treatment beam, the first treatment beam being conveyed through the optical fiber and directed into the dermal layer, the wavelength and energy of the first treatment beam being selected to cause collagen shrinkage within the dermal layer;
applying a second treatment beam to the external surface of the skin during application of the first treatment beam to the dermal layer, the wavelength and energy of the second treatment beam being selected to cause collagen shrinkage within the dermal layer; and
detecting radiation from the surface of the patient's skin above the treatment area, the radiation being indicative of the temperature of the patient's skin within the treatment area, to prevent non-reversible damage to the dermis.

* * * * *